United States Patent
Nita

(10) Patent No.: US 7,297,131 B2
(45) Date of Patent: Nov. 20, 2007

(54) THERAPEUTIC ULTRASOUND SYSTEM

(75) Inventor: Henry Nita, Redwood Shores, CA (US)

(73) Assignee: Flowcardia Inc., Sunnyvale, CA (US)

( * ) Notice: Subject to any disclaimer, the term of this patent is extended or adjusted under 35 U.S.C. 154(b) by 262 days.

(21) Appl. No.: 11/029,678

(22) Filed: Jan. 5, 2005

(65) Prior Publication Data

US 2005/0119606 A1 Jun. 2, 2005

Related U.S. Application Data

(60) Continuation of application No. 11/014,606, filed on Dec. 16, 2004, which is a division of application No. 10/211,418, filed on Aug. 2, 2002, now Pat. No. 6,855,123.

(51) Int. Cl.
*A61B 17/20* (2006.01)

(52) U.S. Cl. ...................................... 604/22

(58) Field of Classification Search ................. 604/22; 606/169, 170, 171; 600/437
See application file for complete search history.

(56) References Cited

U.S. PATENT DOCUMENTS

| | | | |
|---|---|---|---|
| 4,486,680 A | 12/1984 | Bonnet et al. | |
| 4,572,184 A | 2/1986 | Stohl et al. | |
| 4,920,954 A | 5/1990 | Alliger et al. | |
| 5,248,296 A | 9/1993 | Alliger | |
| 5,269,297 A | 12/1993 | Weng et al. | |
| 5,312,328 A | 5/1994 | Nita et al. | |
| 5,342,292 A | 8/1994 | Nita et al. | |
| 5,346,502 A | 9/1994 | Estabrook et al. | |
| 5,382,228 A * | 1/1995 | Nita et al. | 604/22 |
| 5,507,738 A | 4/1996 | Ciervo | |
| 5,989,208 A * | 11/1999 | Nita | 604/22 |
| 6,051,010 A * | 4/2000 | DiMatteo et al. | 606/169 |
| 6,387,109 B1 | 5/2002 | Davison et al. | |

\* cited by examiner

*Primary Examiner*—Kevin C. Sirmons
*Assistant Examiner*—Deanna K. Hall
(74) *Attorney, Agent, or Firm*—Raymond Sun

(57) ABSTRACT

An ultrasound system has a catheter including an elongate flexible catheter body having at least one lumen extending longitudinally therethrough. The catheter further includes an ultrasound transmission member extending longitudinally through the lumen of the catheter body, the ultrasound transmission member having a proximal end connectable to a separate ultrasound generating device and a distal end coupled to the distal end of the catheter body. The distal end of the catheter body is deflectable. The ultrasound system also includes a sonic connector that connects the ultrasound transmission member to an ultrasound transducer. The ultrasound system also provides a method for reverse irrigation and removal of particles.

8 Claims, 7 Drawing Sheets

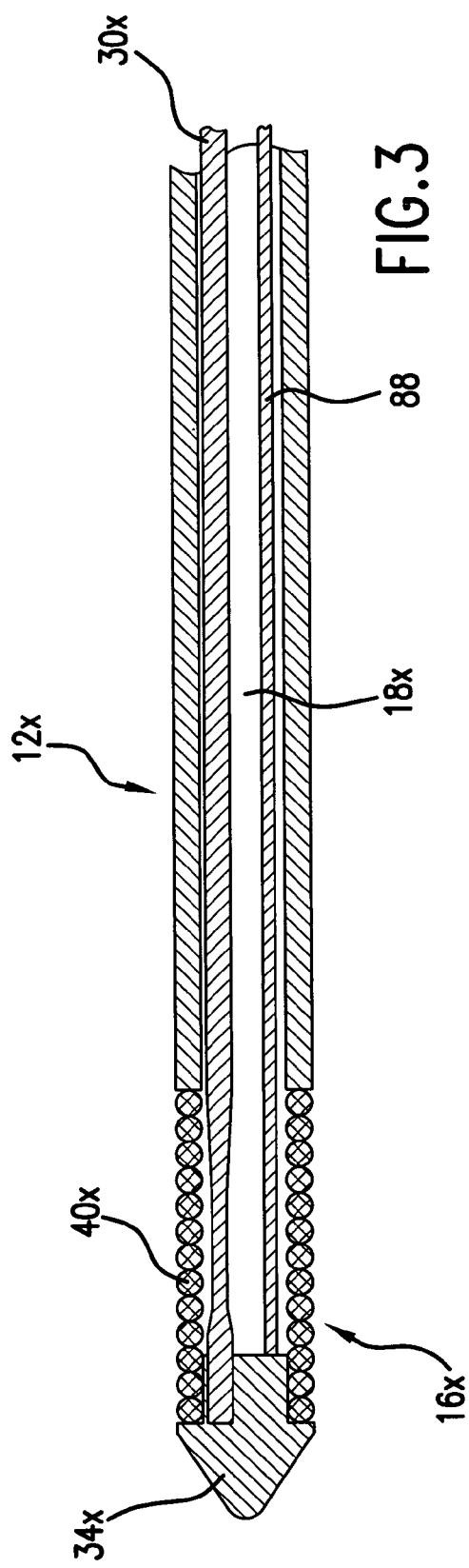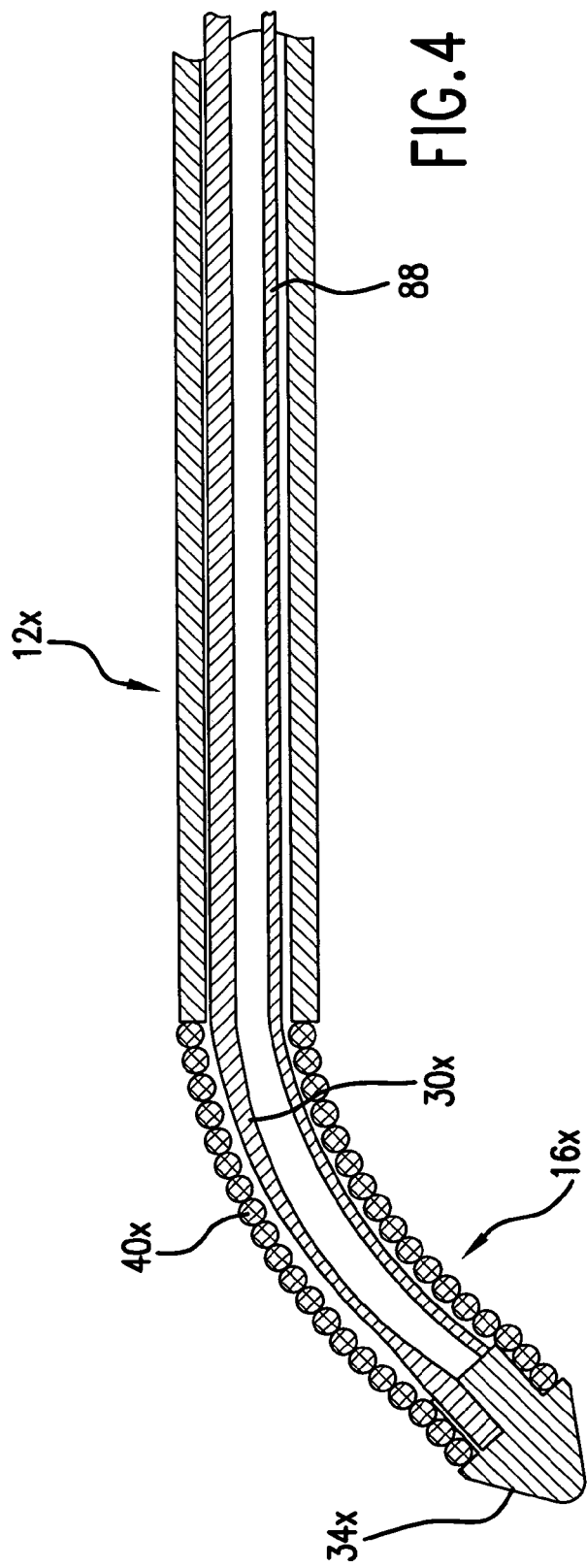

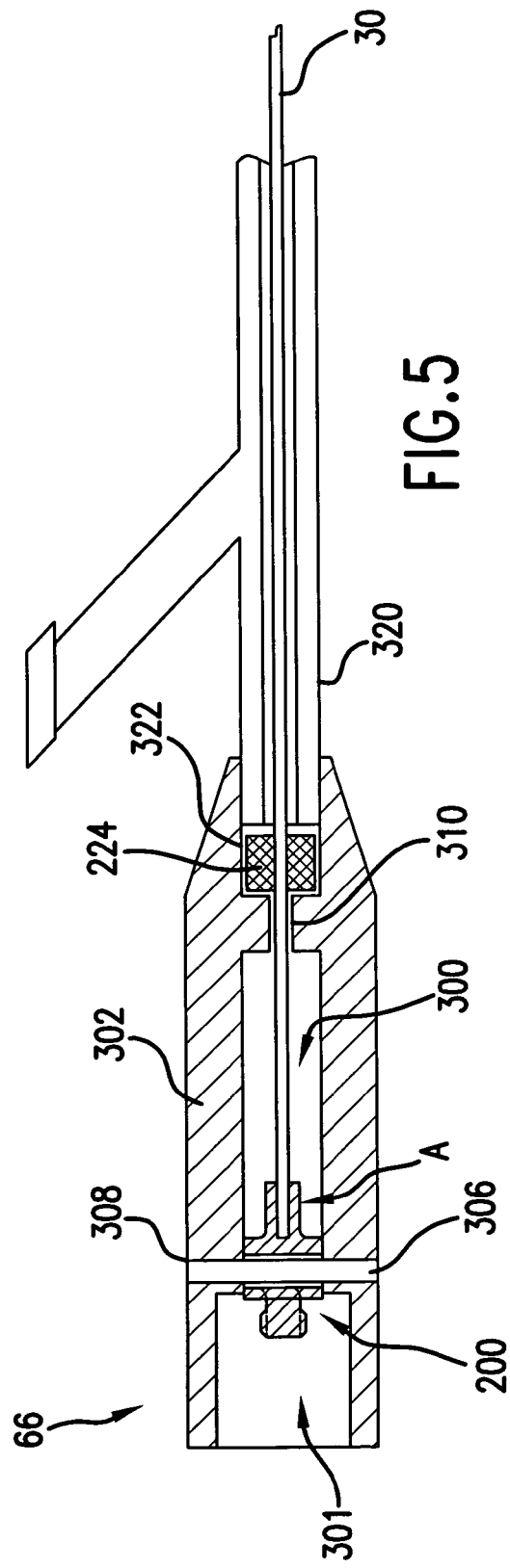
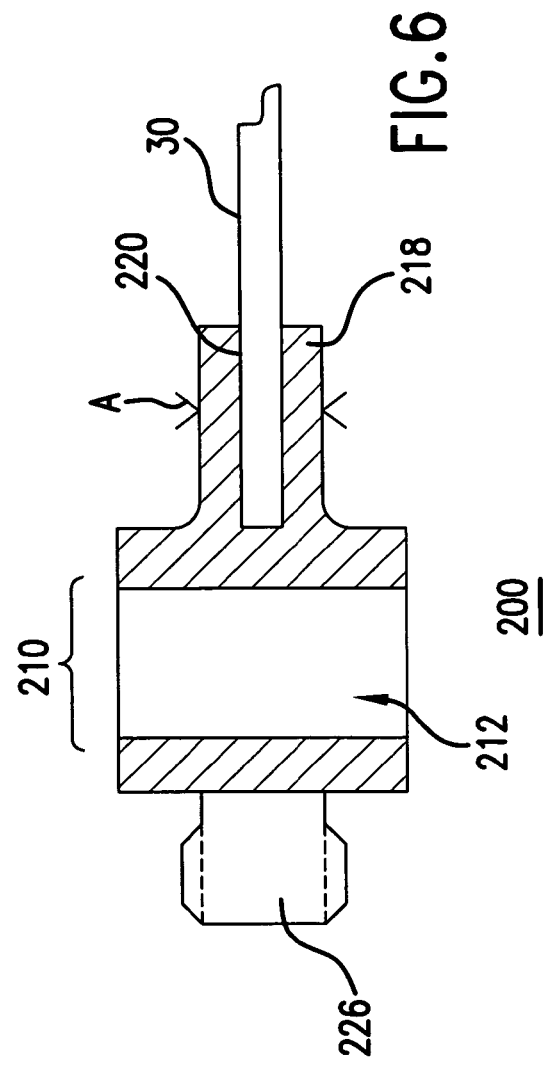

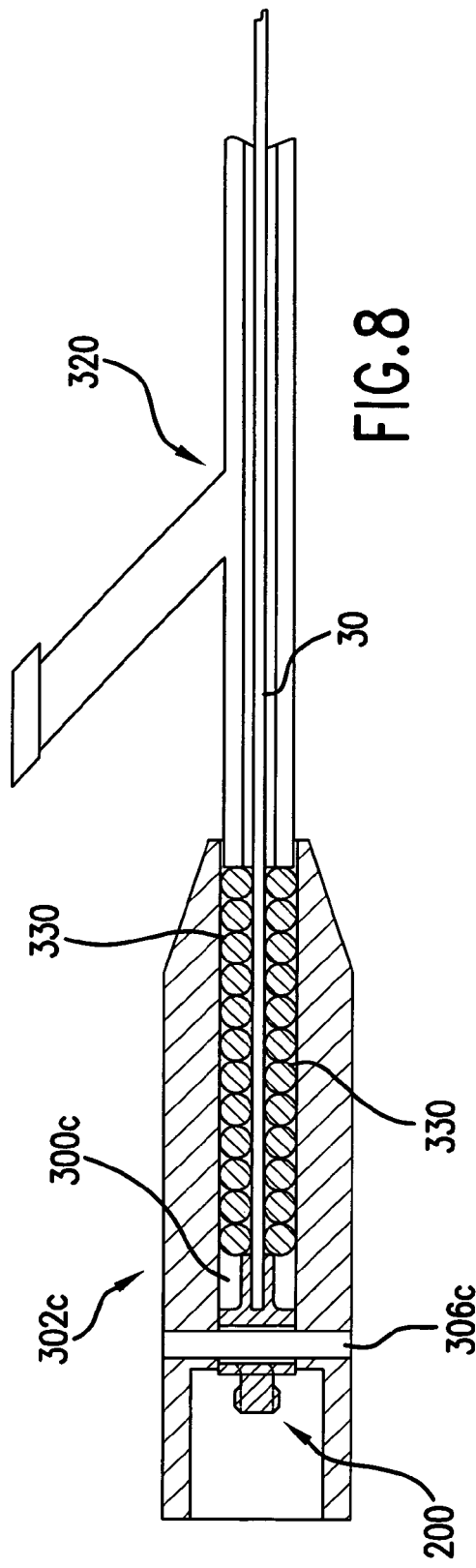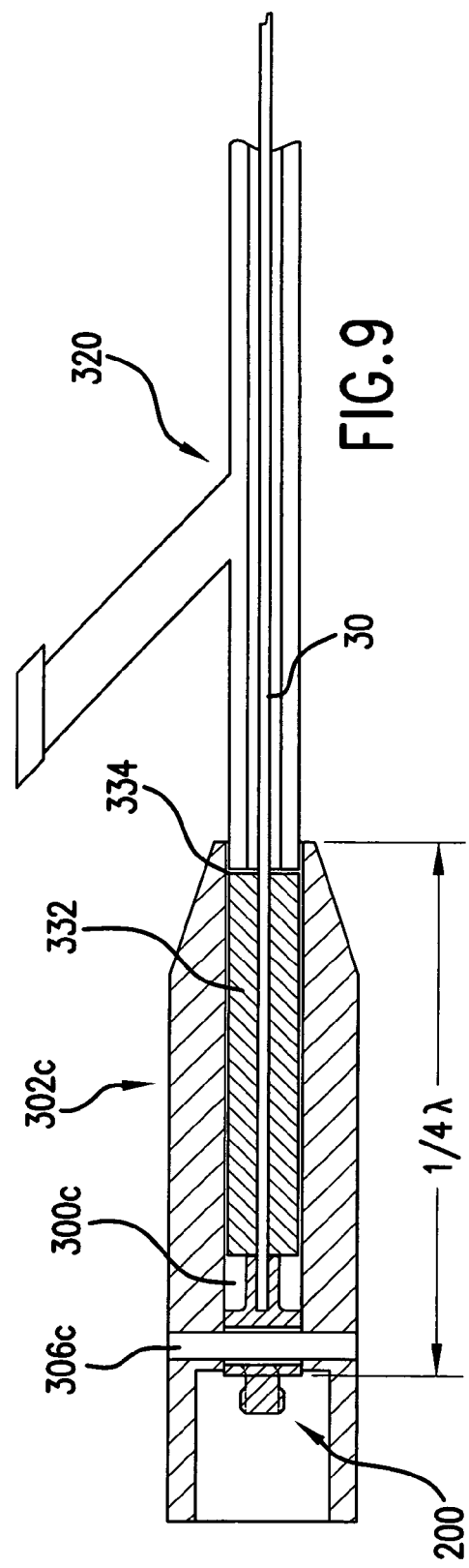

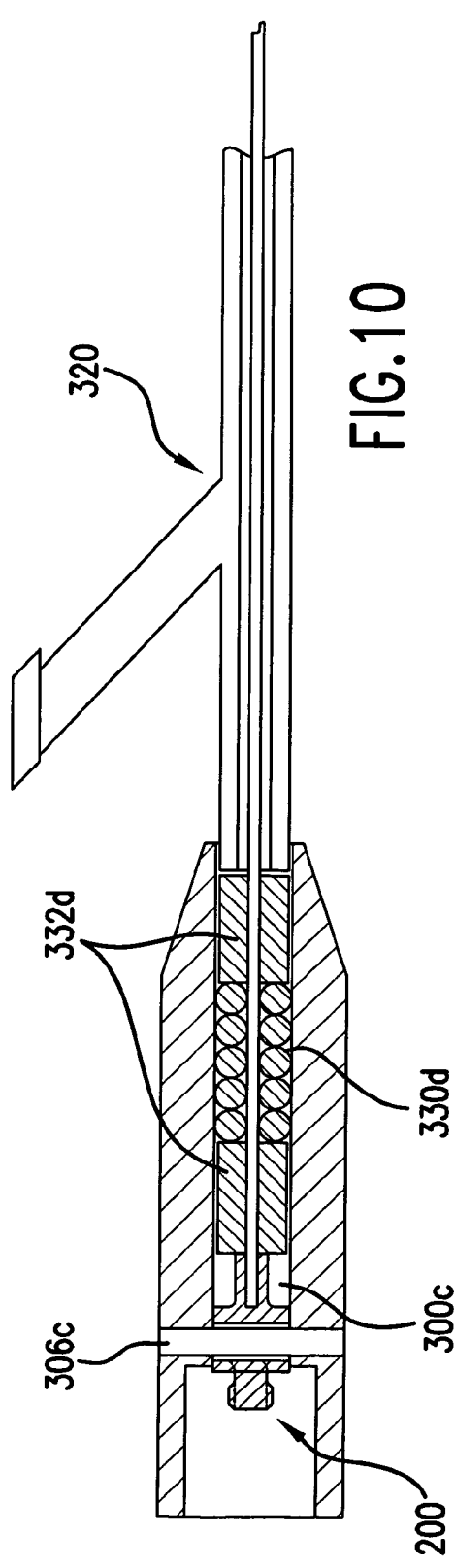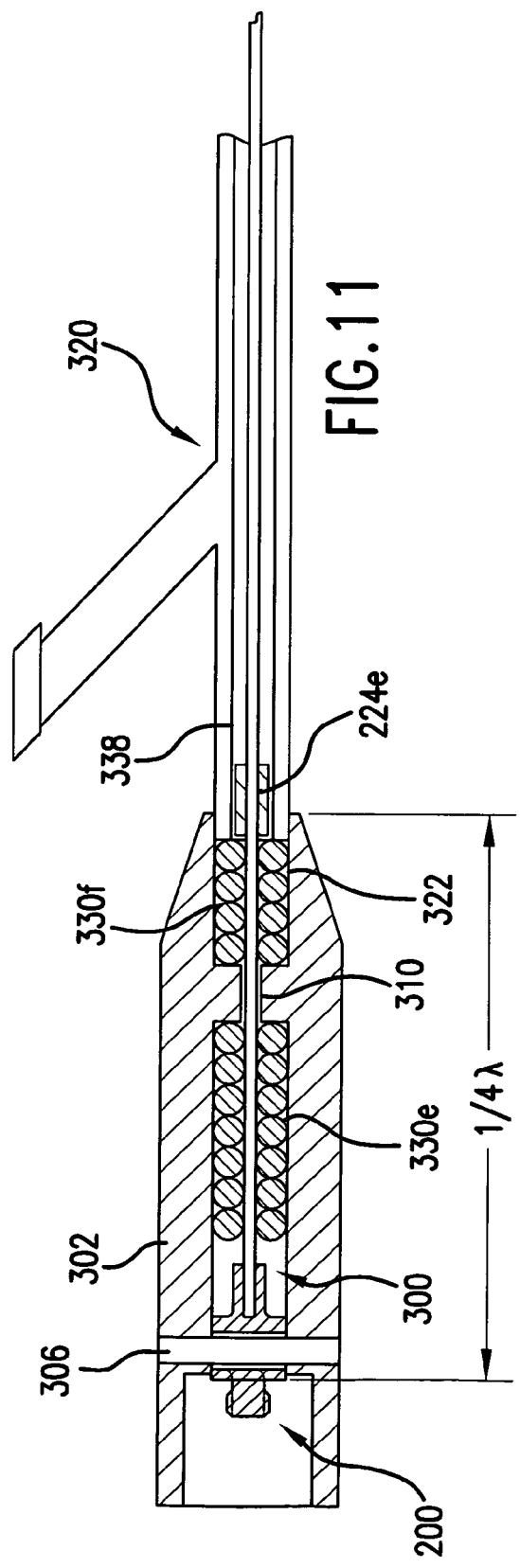

THERAPEUTIC ULTRASOUND SYSTEM

This is a continuation of application Ser. No. 11/014,606, filed Dec. 16, 2004, which is in turn a divisional of Ser. No. 10/211,418, filed on Aug. 2, 2002, now U.S. Pat. No. 6,855,123.

BACKGROUND OF THE INVENTION

1. Field of the Invention

The present invention pertains to medical equipment, and more particularly, to a therapeutic ultrasound system for ablating obstructions within tubular anatomical structures such as blood vessels.

2. Description of the Prior Art

A number of ultrasound systems and devices have heretofore been proposed for use in ablating or removing obstructive material from blood vessels. However, all of these systems and devices generally encounter some problems which are not always adequately addressed by these systems and devices.

A first type of problem relates generally to the effective transmission of ultrasound energy from an ultrasound source to the distal tip of the device where the ultrasound energy is applied to ablate or remove obstructive material. Since the ultrasound source, such as a transducer, is usually located outside the human body, it is necessary to deliver the ultrasound energy over a long distance, such as about 150 cm, along an ultrasound transmission wire from the source to the distal tip. Attenuation of the acoustical energy along the length of the transmission wire means that the energy reaching the distal tip is reduced. To ensure that sufficient energy reaches the distal tip, a greater amount of energy must be delivered along the transmission wire from the source to the distal tip. This transmission of increased energy along the transmission wire may increase the fatigue experienced by the transmission wire at certain critical locations, such as at the connection between the transducer and the transmission wire.

In addition to the above, it is important to be able to conveniently connect and disconnect the ultrasound transmission member from the transducer without creating unnecessary stresses on the ultrasound transmission wire, or weakening the ultrasound transmission wire. Since the transducer is a non-sterile unit, and the ultrasound transmission wire is a sterile unit, a transducer can be used with numerous different ultrasound transmission wires in numerous different procedures. Therefore, there is also a need to provide a removable connection between the ultrasound transmission wire and the transducer that can effectively transmit ultrasound energy while maintaining the integrity of the ultrasound transmission wire.

A second type of problem relates to the need for accurately positioning the ultrasound device inside a patient's vasculature, and in particular, where the vasculature contains smaller and more tortuous vessels. To address this need, flexible and low-profile ultrasound devices have been provided which allow the device to be navigated through small and tortuous vessels. However, these devices have not been completely satisfactory in meeting these navigational needs.

A third type of problem relates to the removal of particles that are produced when the obstructive material is ablated or broken up. It is important that these particles be removed from the patient's vascular system to avoid distal embolization and other clinical complications.

Thus, there still exists a need for improved ultrasound systems having ultrasound devices or catheters which address the aforementioned problems.

SUMMARY OF THE DISCLOSURE

The terms "ultrasound transmission wire" and "ultrasound transmission member" shall be used interchangeably herein, and are intended to mean the same element.

It is an object of the present invention to provide an ultrasound device that provides an improved connection between the ultrasound transmission member and the transducer.

It is another object of the present invention to provide an ultrasound device that has a removable connection between the ultrasound transmission member and the transducer.

It is yet another object of the present invention to provide an ultrasound device with a distal end that can effectively navigate smaller and more tortuous vessels.

It is yet another object of the present invention to provide an ultrasound device that effectively removes particles from the patient's vascular system.

In order to accomplish the objects of the present invention, there is provided an ultrasound system having a catheter including an elongate flexible catheter body having at least one lumen extending longitudinally therethrough. The catheter further includes an ultrasound transmission member extending longitudinally through the lumen of the catheter body, the ultrasound transmission member having a proximal end connectable to a separate ultrasound generating device and a distal end coupled to the distal end of the catheter body. In one embodiment, the distal end of the catheter body is deflectable. The ultrasound system of the present invention can incorporate one of several embodiments of sonic connectors that connect the ultrasound transmission member to an ultrasound transducer. The ultrasound system of the present invention also provides a method for reverse irrigation and removal of particles.

BRIEF DESCRIPTION OF THE DRAWINGS

FIG. 3 is a cross-sectional view of the distal end of another ultrasound catheter that can be used with the system of FIG. 1.

FIG. 4 is a cross-sectional view of the catheter of FIG. 3 shown with the distal end deflected.

FIG. 5 is cross-sectional view of one embodiment of a sonic connector assembly that can be used with the system of FIG. 1.

FIG. 6 is an enlarged cross-sectional view of the sonic connector in FIG. 5.

FIGS. 7-11 are cross-sectional views of different embodiments of sonic connector assemblies that can be used with the system of FIG. 1.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

Figure 1:
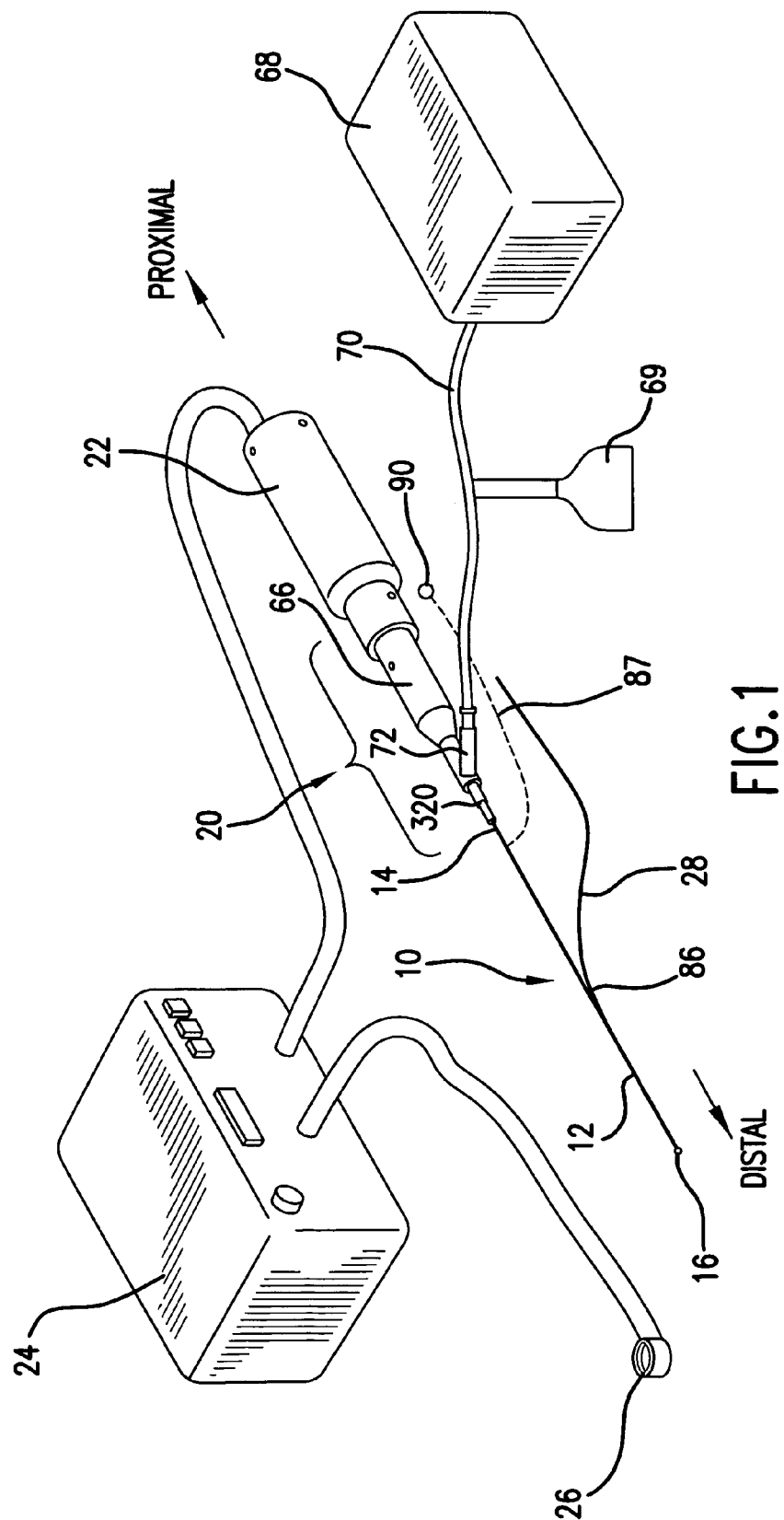
FIG. 1 is a perspective view of an ultrasound system according to the present invention.

FIG. 1 illustrates an ultrasound system according to the present invention for use in ablating and removing occlusive material inside the vessel of an animal or human being. The ultrasound system includes an ultrasonic catheter device 10 which has an elongate catheter body 12 having a proximal end 14, a distal end 16, and defining at least one lumen extending longitudinally therethrough. The ultrasound catheter device 10 is operatively coupled, by way of a proximal connector assembly 20, to an ultrasound transducer 22. The ultrasound transducer 22 is connected to a signal generator 24. The signal generator 24 can be provided with a foot actuated on-off switch 26. When the on-off switch 26 is depressed, the signal generator 24 sends an electrical signal to the ultrasound transducer 22, which converts the electrical signal to ultrasound energy. Such ultrasound energy subsequently passes through the catheter device 10 is delivered to the distal end 16. A guidewire 28 may be utilized in conjunction with the catheter device 10, as will be more fully described below.

Figure 2:
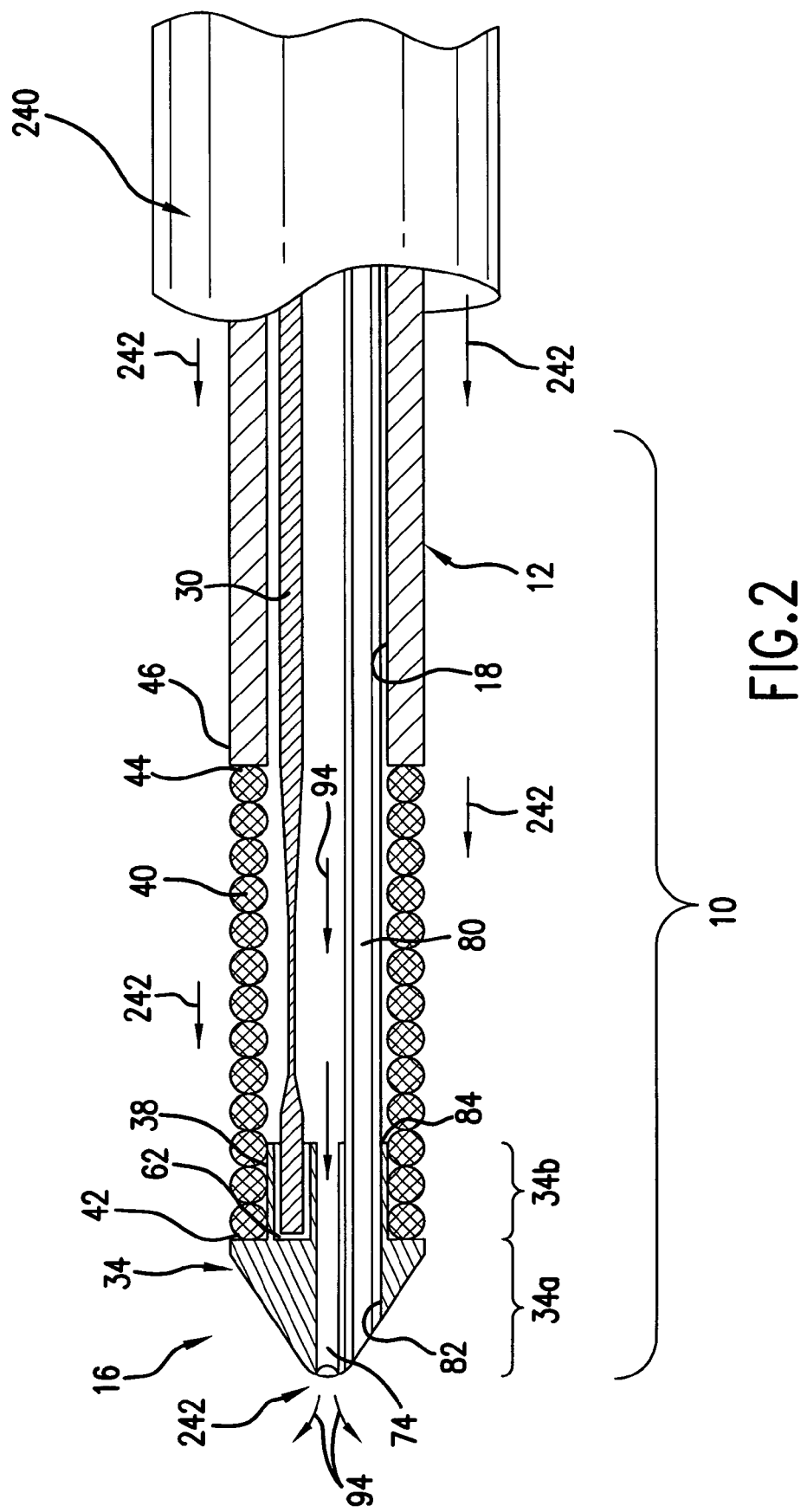
FIG. 2 is a cross-sectional view of the distal end of an ultrasound catheter that can be used with the system of FIG. 1.

FIG. 2 illustrates one non-limiting configuration for the distal end 16 of the catheter body 12 of the catheter device 10. The catheter body 12 is formed of a flexible polymeric material such as nylon (Pebax™) manufactured by Atochimie, Cour be Voie, Hauts Ve-Sine, France. The flexible catheter body 12 is preferably in the form of an elongate tube having one or more lumens extending longitudinally therethrough.

Referring now to FIG. 2, the catheter body 12 has a lumen 18. Extending longitudinally through the lumen 18 of the catheter body 12 is an elongate ultrasound transmission member 30 having a proximal end which is removably connectable to the ultrasound transducer 22 such that ultrasound energy will pass through the ultrasound transmission member 30. As such, when the foot actuated on-off switch 26 operatively connected to the ultrasound transducer 22 is depressed, ultrasound energy will pass through the ultrasound transmission member 30 to the distal end 16 of the catheter body 12. More particularly, the ultrasound transmission member 30 serves to transmit the ultrasound energy from the proximal connector assembly 20 to a distal head 34 mounted on the distal end 16 of the catheter body 12.

The distal head 34 has a substantially rigid member affixed to the distal end 16 of the catheter body 12. In the embodiment shown, the distal head 34 has a generally rounded configuration, and has a proximal portion 34b whose outer diameter is slightly less than the outer diameter of the distal portion 34a of the distal head 34, so as to define an annular shoulder 38 to which a distal end 42 of a coil 40 is attached. The proximal end 44 of the coil 40 is attached to the open distal end 46 of the catheter body 12 such that the proximal portion 34b is not received inside the catheter body 12 but is spaced-apart therefrom. Preferably, the outer diameter of the coil 40 is about the same as the outer diameter of the catheter body 12 and the distal portion 34a, thereby forming a generally smooth outer surface at the juncture of the distal head 34, the coil 40 and the catheter body 12, as shown in FIG. 2.

The attachment of the coil 40 to the distal head 34 and the catheter body 12 may be accomplished by any suitable manner. One manner is through the use of an adhesive which is applied to the interfacing surfaces to be attached. The adhesive may comprise any suitable adhesive, such as cyanoacrylate (e.g., Loctite™ Corp., Ontario, Canada or Aron Alpha™, Borden, Inc., Columbus, Ohio) or polyurethane (e.g., Dymax™, Dymax Engineering Adhesive, Torrington, Conn.). As an alternative to the use of adhesives, various mechanical or frictional connections, such as screw threads, lugs, or other surface modifications formed on one surface, can also be used, with corresponding grooves, detents, or surface modifications formed in the interfacing surface to be attached.

In addition, a guidewire tube 80 defining a guidewire lumen extends through the lumen 18, the coil 40 and a bore 82 formed through the distal head 34. The guidewire tube 80 can be bonded or attached at a location 84 to the bore 82 according to one of the attachment or bonding methods described above. The guidewire tube 80 can extend along the length of the catheter body 12 if catheter device 10 is an "over-the-wire" catheter device. If catheter device 10 is a "monorail" catheter device, as shown in FIG. 1, the guidewire tube 80 terminates at a guidewire aperture 86 adjacent but slightly proximal from the distal end 16 of the catheter body 12, at which the guidewire 28 exits the catheter body 12 (as shown in FIG. 1).

The distal head 34 may be formed of any suitable rigid material, such as metal or plastic. The distal head 34 is preferably formed of radiodense material so as to be easily discernible by radiographic means. Accordingly, the distal head 34 may preferably be formed of metal or, alternatively, may be formed of plastic, ceramic, glass, or rubber materials, optionally having one or more radiodense markers affixed thereto or formed therein. For example, the distal head 34 may be molded of plastic, such as acrylonitrile-butadine-styrene (ABS) and one or more metallic foil strips or other radiopaque markers may be affixed to such plastic distal head 34 in order to impart sufficient radiodensity to permit the distal head 34 to be readily located by radiographic means. Additionally, in embodiments wherein the distal head 34 is formed of molded plastic or other non-metallic material, a quantity of radiodense fillers, such as powdered Bismuth or Barium Sulfate ($BaSO_4$) may be disposed within the plastic or other non-metallic material of which the distal head 34 is formed so as to impart enhanced radiodensity thereto.

The ultrasound transmission member 30 extends through the lumen 18 and the coil 40, and is inserted into a bore 62 which extends longitudinally into the proximal portion 34b of the distal head 34. The distal end of the ultrasound transmission member 30 is firmly held within the bore 62 by the frictional engagement thereof to the surrounding material of the distal head 34, or by other mechanical or chemical affixation means such as but not limited to weldments, adhesive, soldering and crimping. Firm affixation of the ultrasound transmission member 30 to the distal head 34 serves to facilitate direct transmission of the quanta of ultrasonic energy passing through the ultrasound transmission member 30 to the distal head 34. As a result, the distal head 34, and the distal end 16 of the catheter device 10, are caused to undergo ultrasonic vibration in accordance with the combined quanta of ultrasonic energy being transmitted through the ultrasound transmission member 30.

The coil 40 can be a single coil, a braid, a multilead coil, a cross-wound coil, a rounded wire coil, a flat wire coil, or any combination thereof. The coil 40 is preferably elastic and is made of a material having high elongation so as to conform to the configuration of the distal end 16 and to vibrate with the distal head 34 upon application of ultrasound energy. The coil 40 can be embedded inside a polymer jacket or coating, such as but not limited to PTFE, polyurethane, polyamide or nylon. The length of the coil 40 can range from 0.1 to 150 cm. Thus, the coil 40 provides several benefits. First, the coil 40 provides an elastic attachment of the distal head 34 to the catheter body 12. Second, the coil 40 allows the distal head 34 to freely vibrate independent of the catheter body 12. Third, the coil 40 provides an additional connection between the catheter body 12 and the distal head 34 since the coil 40 will hold the distal head 34 to the catheter device 10 in the event that the ultrasound transmission member 30 breaks or fractures.

In the preferred embodiment, the ultrasound transmission member 30 may be formed of any material capable of effectively transmitting the ultrasonic energy from the ultrasound transducer 22 to the distal head 34, including but not necessarily limited to metal, plastic, hard rubber, ceramic, fiber optics, crystal, polymers, and/or composites thereof. In accordance with one aspect of the invention, all or a portion of the ultrasound transmission member 30 may be formed of one or more materials which exhibit super-elasticity. Such materials should preferably exhibit super-elasticity consistently within the range of temperatures normally encountered by the ultrasound transmission member 30 during operation of the catheter device 10. Specifically, all or part of the ultrasound transmission member 30 may be formed of one or more metal alloys known as "shape memory alloys".

Examples of super-elastic metal alloys which are usable to form the ultrasound transmission member 30 of the present invention are described in detail in U.S. Pat. No. 4,665,906 (Jervis); U.S. Pat. No. 4,565,589 (Harrison); U.S. Pat. No. 4,505,767 (Quin); and U.S. Pat. No. 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries, and behavior of specific metal alloys which are super-elastic within the temperature range at which the ultrasound transmission member 30 of the present invention operates, any and all of which super-elastic metal alloys may be usable to form the super-elastic ultrasound transmission member 30.

In particular, the present invention provides an ultrasound transmission member 30, all or part of which may be made of a super-elastic metal alloy which exhibits the following physical properties:

| PROPERTY | UNIT | VALUE |
|---|---|---|
| Nickel | Atomic Weight | Min. 50.50-Max. 51.50 |
| | Weight Percent | Min. 55.50-Max. 56.07 |
| Titanium | % | Remainder |
| Total gas content (O, H, N) | % | 0.15 Max |
| Carbon Content | % | 0.010 Max |
| Maximum Tensile Strength | PSI | 220 K |
| Elongation | % | 10-16 |
| Melting Point | Celcius | 1300-1350 |
| Density | g/cm$^3$ | 6.5 |

This alloy provides an ultrasound transmission member 30 that experiences minimum attenuation of ultrasound energy, and which has the ability to be navigated through the complex bends of tortuous vessels without experiencing any permanent deformation which would otherwise result in transmission losses.

Referring now to FIG. 1, the proximal connector assembly 20 of the catheter device 10 has a Y-connector 320. The frontal portion of the Y-connector 320 is connected to the proximal end 14 of the catheter body 12. The proximal end of the rear portion of the proximal connector assembly 20 is attached to a sonic connector assembly 66 which is configured to effect operative and removable attachment of the proximal end of the ultrasound transmission member 30 to the horn of the ultrasound transducer 22. The sonic connector assembly or apparatus is preferably configured and constructed to permit passage of ultrasound energy through the ultrasound transmission member 30 with minimal lateral side-to-side movement of the ultrasound transmission member 30 while, at the same time, permitting unrestricted longitudinal forward/backward vibration or movement of the ultrasound transmission member 30. A more detailed description of the sonic connector assembly 66, and the operative removable attachment of the ultrasound transmission member 30 to the ultrasound transducer 22, are described below.

In the ultrasound system according to the present invention, an injection pump 68 or IV bag is connected, by way of an infusion tube 70, to an infusion port or sidearm 72 of the Y-connector 320. The injection pump 68 is used to infuse coolant fluid (e.g., 0.9% NaCl solution) into and/or through the catheter device 10, and more particularly into the lumen 18 of the catheter body 12. Such flow of coolant fluid may be utilized to prevent overheating of the ultrasound transmission member 30 extending longitudinally through the lumen 18. Due to the desirability of infusing coolant fluid into the catheter body 12, at least one fluid outflow channel 74 extends longitudinally through the distal head 34 to permit the coolant fluid to flow from the lumen 18 out of the distal end 16 of the catheter body 12. See arrows 94 in FIG. 2. Such flow of the coolant fluid through the lumen 18 serves to bathe the outer surface of the ultrasound transmission member 30, thereby providing for an equilibration of temperature between the coolant fluid and the ultrasound transmission member 30. Thus, the temperature and/or flow rate of coolant fluid may be adjusted to provide adequate cooling and/or other temperature control of the ultrasound transmission member 30.

In addition to the foregoing, the injection pump 68 may be utilized to infuse a radiographic contrast medium into the catheter device 10 for purposes of imaging. Examples of iodinated radiographic contrast media which may be selectively infused into the catheter device 10 via the injection pump 68 are commercially available as Angiovist 370 from Berlex Labs, Wayne, N.J. and Hexabrix from Malinkrodt, St. Louis, Mo.

Although the catheter device 10 in FIG. 1 is illustrated as a "monorail" catheter device, the catheter device 10 can be provided as an "over-the-wire" catheter device without departing from the spirit and scope of the present invention. The structural and operative principles of "monorail" and "over-the-wire" guidewire techniques are well known to those skilled in the art, and are not further discussed herein.

The catheter body 12 illustrated in FIG. 2 is deployed with the use of a guidewire as either a "monorail" or an "over-the-wire" catheter device. On the other hand, the catheter body 12 can be deployed without the use of a guidewire, as illustrated in FIG. 3, where catheter body 12x and its distal end 16x are essentially the same as catheter body 12 and its distal end 16, except that the channel 74, the guidewire tube 80 and the bore 82 are omitted from the distal head 34x. The coils 40x and ultrasound transmission member 30x can be the same as the coils 40 and ultrasound transmission member 30 in FIG. 2. FIG. 3 further illustrates the provision of a deflection wire 88 that extends from the distal head 34x through the lumen 18x and exits the catheter body 12x via an exit port adjacent the proximal end 14 of the catheter body 12x (see FIG. 1). The deflection wire 88 can be rounded or flat, and can be made from a flexible and strong material such as stainless steel or nylon. The deflection wire 88 has a distal end which is secured to the distal head 34x by bonding, welding, fusing and similar mechanisms, and a proximal end that is connected to a stretching knob 90 that is provided at the proximal end of the wire 88. When the knob 90 is pulled, the deflection wire 88 will stretch, thereby causing the distal end 16x to deflect, as shown in FIG. 4. When the pulling motion on the knob 90 is released, the wire 88 will relax and return to its normally straight orientation.

It is also possible to provide a deflecting distal end 16x by shaping the distal end 16 or 16x of the catheter body 12 or 12x. Shaping the distal end 16 or 16x at predetermined angles with respect to the catheter body 12 or 12x provides the same function as deflecting the distal end 16x. According to the present invention, shaping the distal end 16 or 16x can be accomplished by radiofrequency, steam or other heat generated methods. It is important that the shaping or pre-shaping of the distal end 16 or 16x not induce stresses or damage to the ultrasound transmission member 30 or 30x. The shaping of the distal end 16 or 16x can be done prior to the actual medical procedure or can be done by the manufacturer or the physician using shaping techniques that are well-known in the art. The shaped catheter body 12 or 12x can then be re-shaped as desired using the same methods.

The present invention further provides a sonic connector assembly 66 that effectively connects the ultrasound transmission member 30 to the transducer 22 in a manner which reduces step sonic amplification and provides a smooth connection transition of the transmission member 30, thereby reducing the stress and fatigue experienced by the transmission member 30. The sonic connector assembly 66 includes a sonic connector that functions to grip or otherwise retain the proximal end of the ultrasound transmission member 30, and which can be removably connected to the transducer 22. In other words, the sonic connector serves as an attaching element that couples the ultrasound transmission member 30 to the transducer 22. The present invention provides several different embodiments of sonic connectors that can be used with the sonic connector assembly 66. Each of these sonic connectors functions to removably connect an ultrasound catheter to a transducer 22 in a manner which minimizes transverse movement at the connection area while maintaining longitudinal ultrasound energy propagation. In this regard, longitudinal vibrations are desirable, while transverse vibrations may cause breakage in the ultrasound transmission member 30. Since the greatest amount of transverse motion occurs at the connection area between the ultrasound transmission member 30 and the transducer 22, elimination of transverse movements at the connection area between the ultrasound transmission member 30 and the transducer 22 is crucial in protecting the integrity of the ultrasound transmission member 30 and minimizing the potential for breakage of the ultrasound transmission member 30.

In one embodiment illustrated in FIG. 5, the sonic connector assembly 66 has a sonic connector 200 housed inside the proximal bore 300 of a knob housing 302. The sonic connector 200 is enlarged in FIG. 6 for greater clarity. The proximal bore 300 in the knob housing 302 has a rear section 301 that has a proximal opening into which a transducer horn (not shown) may be inserted to engage the sonic connector 200. An enlarged bore 322 is provided at the distal end of the knob housing 302, with the enlarged bore 322 communicating with a channel 310. The structure and characteristics of the knob housing and the transducer horn are well-known in the art, and are not described in greater detail herein. For example, the knob housing and transducer horn can be the same as those illustrated in U.S. Pat. No. 5,989,208 to Nita, whose entire disclosure is incorporated by this reference as though set forth fully herein.

The sonic connector 200 has a central portion 210 having a vertical through-bore 212 which receives a locking pin 306. The locking pin 306 is inserted through an opening 308 in the knob housing 302 and is received inside the through-bore 212 to retain the sonic connector 200 at a pre-determined position inside the proximal bore 300 of the knob housing 302, as best illustrated in FIG. 12 of U.S. Pat. No. 5,989,208. The sonic connector 200 further includes a front shaft 218 extending distally from the central portion 210. The sonic connector 200 also has a threaded stem 226 extending proximally from the central portion 210 to permit the distal end of the transducer horn to be threadably screwed onto and removably attached to the sonic connector 200.

The distal end of the front shaft 218 has a bore 220 that terminates before the central portion 210. The proximal end of the ultrasound transmission member 30 extends through the channel 310 in the knob housing 302 and through the bore 220, and is dimensioned to be snugly fitted inside the bore 220. The proximal end of the ultrasound transmission member 30 is secured inside the inner bore 220 by welding, bonding, crimping, soldering, or other conventional attachment mechanisms. As one non-limiting example, the proximal end of the ultrasound transmission member 30 is crimped to the front shaft 218 at location A.

An intermediate member 224 is seated in the enlarged bore 322 and has a bore that receives (i.e., circumferentially surrounds) the ultrasound transmission member 30. In other words, the intermediate member 224 is positioned between the ultrasound transmission member 30 and the enlarged bore 322. The intermediate member 224 is preferably made of an elastic material, and non-limiting examples include a polymer or rubber. The intermediate member 224 functions to absorb transverse micro-motions, thereby minimizing the undesirable transverse vibrations.

The proximal end of the Y-connector 320 can be threadably engaged to the opening of the enlarged bore 322. Thus, the intermediate member 224 is spaced apart from the crimp location A by a distance of about one-quarter wavelength.

Figure 7:
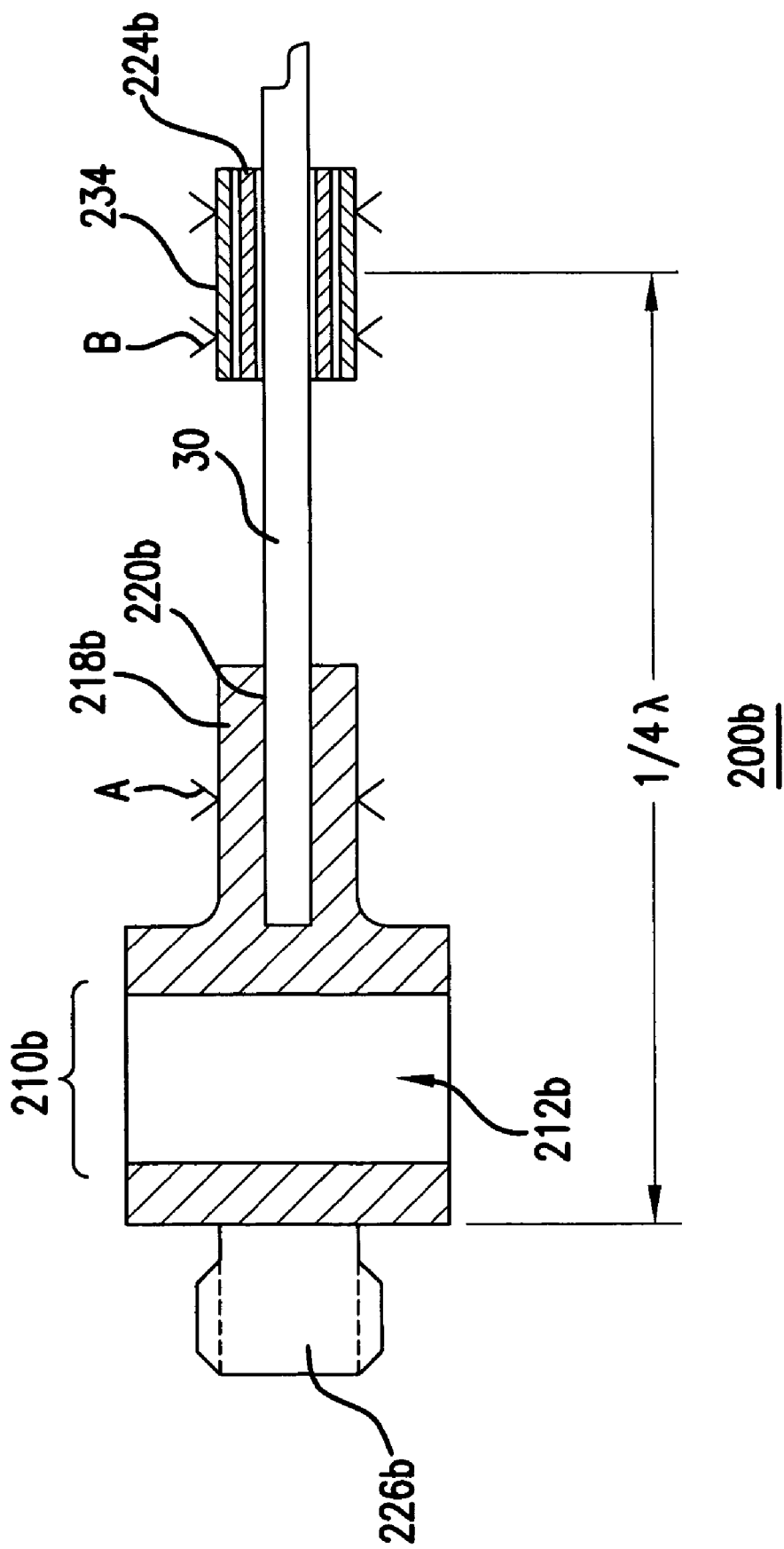

FIG. 7 illustrates another embodiment of a sonic connector 200b that is similar to the sonic connector 200 in FIG. 5. As a result, the same numerals are utilized to designate the same elements in both FIGS. 5 and 7, except that the same element in FIG. 7 includes a "b" in the designation. The sonic connector 200b has a separate tubular member 234 which is spaced-apart from the distal-most end of the front shaft 218b. The tubular member 234 has a bore that retains an intermediate member 224b, which in turn surrounds a portion of the ultrasound transmission member 30. Thus, the intermediate member 224b is now provided inside a tubular member 234 as opposed to being provided in the knob housing 302 (as in FIG. 5). The tubular member 234 can be crimped to the ultrasound transmission member 30. Thus, there are two connection locations A and B in FIG. 7. The crimp location A involves a crimp of the front shaft 218b and the ultrasound transmission member 30. The crimp location B involves a crimp of the tubular member 234, the intermediate member 224b, and the ultrasound transmission member 30. In this manner, these two connection locations actually provide two spaced-apart connection locations, with one location (i.e., B) being separate from the actual sonic connector 200b and acting as a transverse absorber.

The sonic connector is normally attached to the transducer at the highest displacement point of the transducer, which is at the connection with the sonic connector. Studies have shown that one area where the ultrasound transmission member 30 experiences a great amount of stress is about one-quarter wavelength from the connection with the sonic connector. Therefore, the embodiment in FIG. 7 provides a transverse absorber (i.e., 224b) that is positioned at a location along the ultrasound transmission member 30 that is about one-quarter wavelength from the connection with the sonic connector. The configuration in FIG. 7 eliminates a greater amount of transverse energy at the proximal end of the ultrasound transmission member 30, thereby minimizing potential breakage of the ultrasound transmission member 30. In addition, reduced transverse movements propagating towards the distal end of the catheter 10 will result in the generation of less heat so that an ultrasound transmission member 30 with a smaller cross-sectional area can be used. This will in turn result in a more flexible catheter 10 that allows the catheter 10 to run a continuous wave mode (since pulsing is one method of reduce heat). The combined use of a continuous wave mode of operation and pulsing would allow for the ultrasound ablation of a larger variety of tissues (e.g., soft, hard, fibrous).

The intermediate members 224, 224b function as absorbers that minimize undesirable transverse vibrations. To be effective in minimizing transverse vibrations, the absorber needs to be seated tightly around the ultrasound transmission member 30 so as to impact the micro-transverse motions vibrations or motions experienced by the ultrasound transmission member 30. This tight seat, fit or grip is generally accomplished by creating an additional force, or squeezing the absorber against the ultrasound transmission member 30, which can be performed using one of two methods. In a first method, the absorber is squeezed longitudinally. Unfortunately, this longitudinal force may deform the absorber and may create a non-uniform grip which might in turn provide an inconsistent grip around the ultrasound transmission member 30. Fortunately, this inconsistency can be overcome by providing a plurality of O-rings around the ultrasound transmission member 30, as described below in connection with FIG. 8. A second method uses a perpendicular (i.e., transverse) force to compress the absorber around the ultrasound transmission member 30, and the crimping techniques described in FIGS. 5 and 7 herein are examples of this second method.

FIG. 8 illustrates how the sonic connector 200 shown in FIG. 6 can be used with a slightly different knob housing to overcome the inconsistent grip around the ultrasound transmission member 30 provided by a longitudinal gripping force. The knob housing 302c in FIG. 8 is similar to the knob housing 302 in FIG. 5, so the same numerals are utilized to designate the same elements in both FIGS. 5 and 8, except that the same element in FIG. 8 includes a "c" in the designation. In the knob housing 302c, the bore 300c is provided as a single bore, without the channel 310 and the enlarged bore 322. The ultrasound transmission member 30 extends through the Y-connector 320 and into the bore 300c, and a plurality of O-rings 330 are provided around the ultrasound transmission member 30 inside the bore 300c. Thus, the O-rings 330 function like the absorbers 224 and 224b, and are seated tightly around the ultrasound transmission member 30 adjacent the connection area of the ultrasound transmission member 30 and the transducer 22 so as to impact the micro-transverse motions vibrations or motions experienced by the ultrasound transmission member 30 at this location where transverse motion is the greatest. In addition, the length of the combined plurality of O-rings 330 extends across a larger proximal area of the ultrasound transmission member 30 (when compared to the length of the absorbers 224, 224b), so that the embodiment of FIG. 8 is better suited for use in applications where the transverse motions are greater. In contrast, the embodiments in FIGS. 5 and 7 may be better suited for use in applications where the transverse motions are lesser.

FIG. 9 illustrates a modification that can be made to the knob housing 302c in FIG. 8. In the knob housing 302c in FIG. 9, the O-rings 330 are replaced by a single absorber member 332 retained inside the bore 300c and around the ultrasound transmission member 30. The absorber member 332 can have the same features, characteristics and materials as the intermediate members 224 and 224b described above. The length of the absorber member 332 can be provided such the absorber member 332 covers the distance from the distal end 334 of the absorber member 332 to the sonic connector 200, which is about one-quarter wavelength. The embodiment in FIG. 9 shares the same benefits as the embodiment in FIG. 8.

FIG. 10 illustrates another modification that can be made to the knob housings 302c in FIGS. 8 and 9. In particular, a combination of O-rings 330d and absorber members 332d can be retained inside the bore 300c and around the ultrasound transmission member 30. In FIG. 10, a group of O-rings 330d can be positioned between two separate absorber members 332d, although different arrangements of O-rings 330d and absorber members 332d can be utilized as well. The O-rings 330d and absorber members 332d can be the same as the O-rings 330 and absorber member 332 described above. Again, the embodiment in FIG. 10 shares the same benefits as the embodiments in FIGS. 8 and 9.

FIG. 11 illustrates modifications that can be made to the knob housing 302 in FIG. 5, borrowing on the principles illustrated in FIGS. 8-10. The knob housing 302 in FIG. 11 is identical to the knob housing 302 in FIG. 5, so the same numerals are used to designate the same elements of the knob housing 302 in FIGS. 5 and 11. In FIG. 11, a first plurality of O-rings 330e can be retained inside the bore 300 and around the ultrasound transmission member 30, and a second plurality of O-rings 330f can be retained inside the enlarged bore 322 and around the ultrasound transmission member 30. In addition, an intermediate member 224e can be retained inside the bore 338 of the Y-connector 320 (at the connection location between the enlarged bore 322 and the proximal end of the Y-connector 320) and around the ultrasound transmission member 30. The O-rings 330e, 330f and intermediate member 224e can be the same as the O-rings 330 and intermediate member 224 described above. The distance from the intermediate member 224e to the sonic connector 200 can be about one-quarter wavelength.

The provision of the sonic connectors and knob housings illustrated in FIGS. 5 and 7-11 are so effective in reducing stresses on the ultrasound transmission member 30 that they facilitate the use of a deflectable distal end 16x as described hereinabove. Previously-known ultrasound catheters have not been able to enjoy the luxury of a deflectable distal end because any bending at the distal end of the ultrasound transmission member 30 would cause the ultrasound transmission member 30 to bend too, thereby adding to the stresses already experienced by the ultrasound transmission member 30, resisting longitudinal propagation of ultrasound energy, and creating an additional source of heat, all of which would increase the potential of breakage of the ultrasound transmission member 30. Thus, the implementation of the sonic connectors illustrated in FIGS. 5 and 7-11 allows for the distal end of the ultrasound transmission member 30 to be bent without experiencing many of these drawbacks.

The present invention further provides for reverse irrigation to remove particles that have been ablated during the ultrasound procedure. Referring to FIG. 2, irrigation fluid can be injected through a guiding catheter 240 (and along the outer surface of the catheter body 12) as shown by the arrows 242. The irrigation fluid will travel to the distal head 34 of the catheter 10, and will carry the particles through the channel 74 in a reverse direction (i.e., from distal to proximal) and through the lumen 18. The irrigation fluid and particles will travel in a proximal direction along the lumen 18 to the infusion tube 70, and is collected into a bottle or container 69 that can be connected to the infusion tube 70. During this operation, the injection pump 68 can serve as a negative pressure pump.

As yet a further alternative, particles can be removed by applying a vacuum to remove the particles via the lumen of the guidewire tube 80. For example, in an "over-the-wire" catheter embodiment, particles can be removed via the lumen of the guidewire tube 80 using a pump or a syringe.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An ultrasound catheter comprising:
an elongate flexible catheter body having a proximal end, a distal end and at least one lumen extending longitudinally therethrough;
an ultrasound transmission member extending longitudinally through the lumen of the catheter body, the ultrasound transmission member transmitting ultrasound energy having node points;
a sonic connector positioned on the proximal end of the ultrasound transmission member for connecting the ultrasound transmission member to a separate ultrasound generating device, the sonic connector comprising a proximal section for connection to a separate ultrasound generating device, and a front portion having a bore which receives the proximal end of the ultrasound transmission member; and
an absorber positioned on the proximal end of the ultrasound transmission member and between the sonic connector and a first node point, the absorber surrounding the ultrasound transmission; and
wherein the sonic connector and the ultrasound transmission member are crimped together at a first location, and the absorber and the ultrasound transmission member are crimped together at a second location.

2. The catheter of claim 1, wherein the first and second locations are spaced apart by a distance of about one-quarter wavelength.

3. The catheter of claim 1, wherein the absorber includes a plurality of O-rings.

4. The catheter of claim 1, wherein the absorber includes at least two different absorbers positioned adjacent to each other.

5. The catheter of claim 1, wherein the absorber includes a first absorber and a second absorber, with the first absorber spaced apart from the second absorber.

6. The catheter of claim 5, wherein the absorber further includes a third absorber that is positioned adjacent to the second absorber.

7. An ultrasound catheter comprising:
an elongate flexible catheter body having a proximal end, a distal end and at least one lumen extending longitudinally therethrough;
an ultrasound transmission member extending longitudinally through the lumen of the catheter body, the ultrasound transmission member transmitting ultrasound energy having node points;
a sonic connector positioned on the proximal end of the ultrasound transmission member for connecting the ultrasound transmission member to a separate ultrasound generating device at a connection location, the sonic connector comprising a proximal section for connection to a separate ultrasound generating device, and a front portion having a bore which receives the proximal end of the ultrasound transmission member; and
means substantially surrounding the proximal end of the ultrasound transmission member and positioned between the sonic connector and a first node point for absorbing transverse motions of the ultrasound transmission member;
wherein the absorbing means is a single component and is positioned within an area of one-quarter wavelength from the sonic connector.

8. An ultrasound catheter comprising:
an elongate flexible catheter body having a proximal end, a distal end and at least one lumen extending longitudinally therethrough;
an ultrasound transmission member extending longitudinally through the lumen of the catheter body, the ultrasound transmission member transmitting ultrasound energy having node points;
a sonic connector positioned on the proximal end of the ultrasound transmission member for connecting the ultrasound transmission member to a separate ultrasound generating device at a connection location, the sonic connector comprising a proximal section for connection to a separate ultrasound generating device, and a front portion having a bore which receives the proximal end of the ultrasound transmission member; and
means substantially surrounding the proximal end of the ultrasound transmission member and positioned between the sonic connector and a first node point for absorbing transverse motions of the ultrasound transmission member;
wherein the absorbing means has two or more components and is positioned within an area of one-quarter wavelength from the sonic connector.

* * * * *